United States Patent [19]
Lavielle et al.

[11] Patent Number: 6,020,336
[45] Date of Patent: Feb. 1, 2000

[54] INDOLE AND INDAZOLE COMPOUNDS

[76] Inventors: Gilbert Lavielle, 1 avenue Lilly, F-78170 La Celle Saint Cloud; Olivier Muller, 12 Place du Noyer, F-95300 Ennery; Christine Vayssettes-Courchay, 15 rue Jean Tassel, F-91430 Igny; Jean-Jacques Descombes, 45 rue Châteaubriand, F-92500 Rueil Malmaison; Tony Verbeuren, 60 bis rue Aristide Briand, F-78540 Vernouillet, all of France

[21] Appl. No.: 09/146,009

[22] Filed: Sep. 2, 1998

[30] Foreign Application Priority Data

Sep. 3, 1997 [FR] France .................................. 97 10939

[51] Int. Cl.[7] ...................... A61K 31/425; A61K 31/495; C07D 403/10; C07D 403/04
[52] U.S. Cl. .......................... 514/253; 514/254; 514/383; 514/322; 514/323; 544/295; 544/357; 544/364; 544/366; 544/370; 548/266.4; 546/199; 546/201
[58] Field of Search .................... 544/295, 357, 544/364, 366, 370, 372, 374; 548/266.4; 514/253, 254, 383

[56] References Cited

U.S. PATENT DOCUMENTS 5,807,857  9/1998  Castro Pineiro et al. .............. 514/253
5,834,502  11/1998  Cheng et al. ............................ 514/383
5,854,268  12/1998  Baker et al. ............................. 514/383

OTHER PUBLICATIONS

Angiology, The Journal of Vascular Diseases, vol. 48, No. 7, Jul. 1997, pp. 559–567.
State of the Art in Chronic Venous Insufficiency, La Presse Medicale, Feb. 10, 1994, vol. 23, No. 5, pp. 196–201.

Primary Examiner—Mukund J. Shah
Assistant Examiner—Ann M. Kessinger

[57] ABSTRACT

Compound of formula (I):

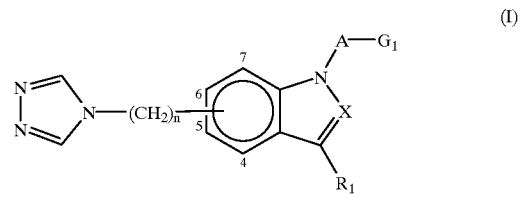

wherein:
n is 0 or 1,
A represents a σ bond or alkylene or alkenylene,
X represents nitrogen or C—$R_2$,
$R_1$ represents hydrogen or alkyl, and
$G_1$ represents any one of the groups defined in the description and medicaments containing the same.

17 Claims, No Drawings

INDOLE AND INDAZOLE COMPOUNDS

TITLE OF THE INVENTION

The present invention relates to a new indole and indazole compounds, to a process for their preparation and to pharmaceutical compositions containing them.

DESCRIPTION OF THE PRIOR ART

Many indole compounds have been described in the literature. A number of them have been studied for their $5\text{-HT}_{1D}\text{-}5\text{-}_{1\text{-}like}$ agonist properties. There may be mentioned by way of example Applications WO 97/11675, WO 97/06159, WO 96/04269 and GB 2289465. Patent EP 135 781 describes indazole compounds as central analgesics having neuroleptic properties.

BACKGROUND OF THE INVENTION

Serotonin (5-HT) receptors have been subdivided into seven main families, of which the $5\text{-HT}_1$ receptor family forms a heterogeneous group in which a number of receptors have not yet been properly characterised.

Sumatriptan, an anti-migraine agent, interacts with $5\text{-HT}_1$ receptors which have been described as being type $5\text{-HT}_{1B}$, $5\text{-HT}_{1D}$ or $5\text{-HT}_{1\text{-}like}$ (Sumner et al., Brit. J. Pharmacol., 105, 603, 1992, Olesen, La Recherche, 23, 160, 1992). The selectivity of sumatriptan for those $5\text{-HT}_{1B}$, $5\text{-HT}_{1D}$ and $5\text{-HT}_{1\text{-}like}$ receptors has been proposed as the main reason for its anti-migraine activity (Macon et al., J. Med. Chem., 37, 2509, 1994), in which selective vasoconstriction of the carotid vascular bed is involved (Saxena et al. T.I.P.S., 10, 200, 1989). Such receptors, which are present in the venous system, are also found in the brain, and their activation or inhibition may be at the origin of certain disorders of the central nervous system (Clitherow et al., J. Med. Chem, 37, 2253, 1994).

The compounds of the present invention have a novel structure by virtue especially of the presence of an aminated side chain that substitutes the heterocyclic nitrogen atom and of a triazole structure that substitutes the aromatic nucleus. That structure, surprisingly, provides the compounds of the invention with a high selectivity for the $5\text{-HT}_{1B}$, $5\text{-HT}_{1D}$ and $5\text{-HT}_{1\text{-}like}$ receptors. They are thus able to be used as a venotonic agent in the treatment of venous insufficiency and of associated disorders, and also in the treatment of migraine and conditions associated with that disorder, "cluster headaches", pain, migraine associated with vascular disorders, and in hypertension, obesity and eating disorders.

The activity of the compounds of the invention has been evaluated in a pharmacological test that measures their potential for contracting the saphenous vein isolated from a dog or rabbit, as described by Humphrey et al. (Br. J. Pharmacol., 94, 1123, 1988).

DETAILED DESCRIPTION OF THE INVENTION

The present invention relates to compounds of formula (I):

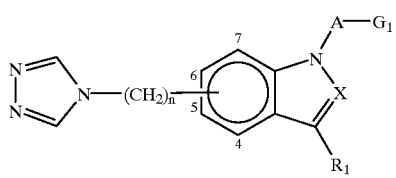

wherein:

n is 0 or 1,

A represents a σ bond or a linear or branched $(C_1\text{-}C_8)$ alkylene group or a linear or branched $(C_1\text{-}C_8)$ alkenylene group, X represents a nitrogen atom or a C—$R_2$ group wherein $R_2$ represents a hydrogen atom or a linear or branched $(C_1\text{-}C_6)$alkyl group, $R_1$ represents a hydrogen atom or a linear or branched $(C_1\text{-}C_6)$alkyl group, $G_1$ represents a pyrrolidinyl or piperidyl group, each of those groups being optionally substituted on any of the junctions of the ring by a linear or branched $(C_1\text{-}C_6)$ alkyl group, $(C_3\text{-}C_7)$cycloalkyl group, $(C_3\text{-}C_7)$ cycloalkyl-$(C_1\text{-}C_6)$alkyl group in which the alkyl is linear or branched, nitrile group, carboxy group, linear or branched $(C_1\text{-}C_6)$alkoxycarbonyl group, carbamoyl group (optionally substituted by one or two linear or branched $(C_1\text{-}C_6)$alkyl, $(C_3\text{-}C_7)$cycloalkyl, optionally substituted phenyl and/or optionally substituted benzyl groups), optionally substituted aryl group, optionally substituted aryl-$(C_1\text{-}C_6)$alkyl group in which the alkyl is linear or branched, optionally substituted heteroaryl group or optionally substituted heteroaryl-$(C_1\text{-}C_6)$ alkyl group in which the alkyl is linear or branched, it being understood that those pyrrolidine and piperidine groups may be bonded to A by any one of the atoms of the ring, or $G_1$ represents a group

wherein:

$R_3$ and $R_4$ each independently of the other represent a hydrogen atom, or a linear or branched $(C_1\text{-}C_6)$alkyl group, $(C_3\text{-}C_7)$cycloalkyl group, $(C_3\text{-}C_7)$cycloalkyl-$(C_1\text{-}C_6)$-alkyl group in which the alkyl is linear or branched, optionally substituted aryl-$(C_1\text{-}C_6)$alkyl group in which the alkyl is linear or branched or optionally substituted aryl group, or, together with the nitrogen atom that carries them, form a group:

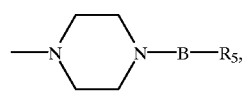

wherein B represents a σ bond or a linear or branched $(C_1\text{-}C_6)$alkylene group and $R_5$ represents a hydrogen atom or a linear or branched $(C_1\text{-}C_6)$alkyl group, $(C_3\text{-}C_7)$-cycloalkyl group, optionally substituted aryl group, optionally substituted aryl-$(C_1\text{-}C_6)$-alkyl group in which the alkyl is linear or branched, optionally substituted heteroaryl group or optionally substituted heteroaryl-($C_1$–$C_6$)alkyl group in which the alkyl is linear or branched, their enantiomers and diastereoisomers, and addition salts thereof with a pharmaceutically acceptable acid or base.

"Aryl group" is understood to mean a group selected from phenyl and naphthyl.

"Heteroaryl group" is understood to mean a group selected from furyl, thienyl, pyridyl, pyrrolyl, imidazolyl, tetrazolyl, pyrazinyl and pyrimidinyl.

The term optionally substituted applied to the terms "phenyl", "benzyl", "aryl", "arylalkyl", "heteroaryl" and "heteroarylalkyl" means that the groups in question are substituted by one or more halogen atoms and/or linear or branched ($C_1$–$C_6$)alkyl, linear or branched ($C_1$–$C_6$)alkoxy, hydroxy and/or linear or branched ($C_1$–$C_6$)trihaloalkyl groups.

Amongst the pharmaceutically acceptable acids, there may be mentioned by way of non-limiting example hydrochloric acid, hydrobromic acid, sulphuric acid, phosphonic acid, glutaric acid, fumaric acid, tartaric acid, maleic acid, citric acid, ascorbic acid, methanesulphonic acid, camphoric acid, oxalic acid, etc.

Amongst the pharmaceutically acceptable bases, there may be mentioned by way of non-limiting example sodium hydroxide, potassium hydroxide, triethylamine, tert-butylamine, etc.

Advantageously, the present invention relates to compounds of formula (I) wherein the triazolyl or triazolylmethyl group is attached to the 6-position of the indole or indazol group.

A further advantageous aspect of the invention relates to compounds of formula (I) wherein the triazolyl or triazolylmethyl group is attached to the 5-position of the indole or indazole group.

The preferred compounds of the invention are those wherein n is 0.

The invention relates preferably to compounds of formula (I) wherein X represents a $CR_2$ group, $R_2$ preferably being a hydrogen atom.

Other preferred compounds of formula (I) are those wherein X represents a nitrogen atom.

In the compounds of formula (I), $R_1$ preferably represents a hydrogen atom.

Preferably the invention relates to compounds of formula (I) wherein, in the substituent A—$G_1$, A represents a σ bond or a linear or branched ($C_1$–$C_6$)alkylene group, and $G_1$ represents a pyrrolidinyl (for example 3-pyrrolidinyl), piperidyl (for example 4-piperidyl) or 1-piperazinyl group, those groups being substituted or unsubstituted. Amongst the preferred substituents, there may be mentioned advantageously the following groups: linear or branched ($C_1$–$C_6$) alkyl, aryl, aryl-($C_1$–$C_6$)alkyl in which the alkyl is linear or branched, heteroaryl and/or heteroaryl-($C_1$–$C_6$)-alkyl in which the alkyl is linear or branched. The pyrrolidinyl and piperidyl groups are advantageously substituted on the nitrogen atom.

A further preferred aspect of the invention relates to compounds of formula (I) wherein A represents a linear or branched ($C_1$–$C_6$)alkylene group and $G_1$ represents a group

wherein $R_3$ and $R_4$ each independently of the other represent a hydrogen atom, or a linear or branched ($C_1$–$C_6$)alkyl group, ($C_3$–$C_7$)-cycloalkyl group, ($C_3$–$C_7$)cycloalkyl-($C_1$–$C_6$)alkyl group in which the alkyl is linear or branched, optionally substituted aryl-($C_1$–$C_6$)alkyl group in which the alkyl is linear or branched or optionally substituted aryl group. Advantageously $R_3$ and $R_4$ represent a linear or branched ($C_1$–$C_6$)alkyl group.

More especially, the invention relates to compounds of formula (I) wherein the triazolyl or triazolylmethyl group is attached to the 6-position of the indole or indazole group, X represents a —CH-group or a nitrogen atom, $R_1$ represents a hydrogen atom, A represents a σ bond or a linear or branched ($C_1$–$C_6$)alkylene group, whilst $G_1$ represents a pyrrolidinyl or piperidinyl group optionally substituted on any of the junctions of the ring by a linear or branched ($C_1$–$C_6$)alkyl group, optionally substituted aryl group, optionally substituted aryl-($C_1$–$C_6$)alkyl group in which the alkyl is linear or branched, optionally substituted heteroaryl group or optionally substituted heteroaryl-($C_1$–$C_6$)alkyl group in which the alkyl is linear or branched, or $G_1$ represents a 1-piperazinyl group optionally substituted on the nitrogen atom in the 4-position by a linear or branched ($C_1$–$C_6$)alkyl group, optionally substituted aryl group, optionally substituted aryl-($C_1$–$C_6$)alkyl group in which the alkyl is linear or branched, optionally substituted heteroaryl group or optionally substituted heteroaryl-($C_1$–$C_6$)alkyl group in which the alkyl is linear or branched, or A represents a linear or branched ($C_1$–$C_6$)alkylene group whilst $G_1$ represents a group

wherein $R_3$ and $R_4$ each independently of the other represent a hydrogen atom or a linear or branched ($C_1$–$C_6$)alkyl group.

The invention relates also to a process for the preparation of the compounds of formula (I), characterised in that, when, in the desired compound of formula (I), X represents a C—$R_2$ group, there is used as starting material a compound of formula (II/a):

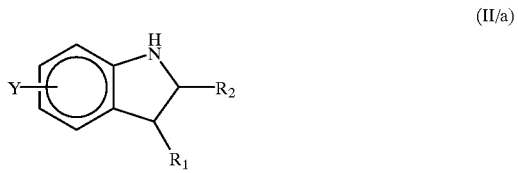

(II/a)

wherein $R_1$ and $R_2$ are as defined for formula (I), and Y represents a nitro group if, in the desired compound of formula (I), n is 0, or Y represents a hydroxymethyl group if, in the desired compound of formula (I), n is 1, which is condensed.

either with a compound of formula (III/a):

Z—A—$G_1$ (III/a)

wherein A and $G_1$ are as defined for formula (I) and Z represents a halogen atom or a formyl group, to yield a compound of formula (IV):

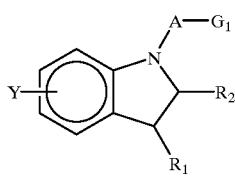

(IV)

wherein A, Y, $G_1$, $R_1$ and $R_2$ are as defined hereinabove, which is subjected to an oxidation reaction to yield a compound of formula (V/a):

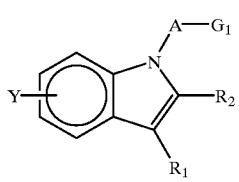

(V/a)

wherein A, Y, $G_1$, $R_1$ and $R_2$ are as defined hereinabove, and the $G_1$ group, when it represents a pyrrolidinyl, piperidinyl or piperazinyl group, is, if desired, substituted on the nitrogen atom in a basic medium or by a reductive amination reaction with a carbonyl compound, or with a compound of formula (III/b), in a basic medium:

 Br—A—OH (III/b)

wherein A is as defined hereinabove, to yield a compound of formula (IV'):

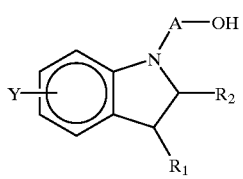

(IV')

wherein Y, A, $R_1$ and $R_2$ are as defined hereinabove, which, after bromination and oxidation, is condensed with a compound of formula $G_1H$, $G_1$ being as defined for formula (I), to yield a compound of formula (V/a), as defined hereinabove,
or,
when, in the desired compound of formula (I), X represents a nitrogen atom, there is used as starting material a compound of formula (II/b):

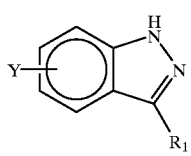

(II/b)

wherein Y and $R_1$ are as defined hereinabove, which is condensed
either with a compound of formula (III/c), in a basic medium:

 Hal—A—$G_1$ (III/c)

wherein A and $G_1$ are as defined hereinabove, and Hal represents a halogen atom, to yield a compound of formula (V/b):

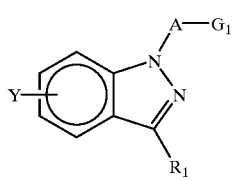

(V/b)

wherein A, Y, $G_2$ and $R_1$ are as defined hereinabove, and the $G_1$ group, when it represents a pyrrolidinyl, piperidyl and piperazinyl group, is, if desired, substituted on the nitrogen atom in a basic medium or by a reductive amination reaction with a carbonyl compound, or with a compound of formula (III/b) as defined hereinabove, to yield a compound of formula (VI):

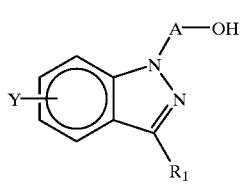

(V)

wherein Y, A and $R_1$ are as defined hereinabove, which, after bromination, is condensed with a compound of formula $HG_1$, $G_1$ being as defined for formula (I), to yield a compound a formula (V/b) as defined hereinabove, which compounds of formulae (V/a) and (V/b) constitute the totality of the compounds of formula (V):

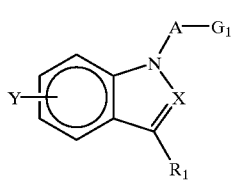

(V)

wherein X, Y, A, $R_1$ and $G_1$ are as defined for formula (I), and Y is as defined hereinabove,
which, by reduction of the Y group (when Y represents a hydroxymethyl group, after conversion to an azido compound), yields a compound of formula (VII):

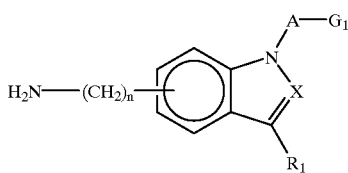

(VII)

wherein n, X, A, $G_1$ and $R_1$ are as defined hereinabove, which is condensed with N,N-dimethylformamide azine, in an acidic medium, to yield the compounds of formula (I), which are optionally purified in accordance with a conventional purification technique, optionally separated into their enantiomers in accordance with a conventional separation technique, and converted, where appropriate, into addition salts thereof with a pharmaceutically acceptable acid or base, it being understood that when Y contains a hydroxy group, it can be protected or deprotected depending on the reagents used.

The invention relates also to pharmaceutical compositions that comprise as active ingredient at least one compound of formula (I) on its own or in combination with one or more inert, non-toxic, pharmaceutically acceptable excipients of carriers. Amongst the pharmaceutical compositions according to the invention, there may be mentioned more especially those that are suitable for oral, parenteral or nasal administration, tablets or dragées, sublingual tablets, gelatin capsules, lozenges, suppositories, creams, ointments, dermal gels, etc.

The useful dosage varies according to the age and weight of the patient, the nature and severity of the disorder, and the route of administration, which may be nasal, rectal, parenteral or oral. The unit does generally ranges from 1 to 500 mg for treatment in from 1 to 3 administrations per 24 hours.

The following Examples illustrate the invention and do not limit it in any way. The structures of the compounds described have been confirmed by the customary spectroscopic techniques.

EXAMPLE 1

1-(N-tert-butyloxycarbonyl-pyrrolidin-3-ylmethyl)-6-([1,2,4]triazol-4-yl)indole

Step a: 1-(N-tert-butyloxycarbonyl-pyrrolidin-3-ylmethyl)-6-nitro-2,3-dihydroindole 91.5 mmol (19.4 g) of solid sodium triacetoxyborohydride are added slowly, at 20° C., to a solution of 60.8 mmol (12.1 g) of 1-(tert-butyloxycarbonyl)-3-formylpyrrolidine, 60.8 mmol (10 g) of 6-nitroindoline and 60.8 mmol (3.65 g) of acetic acid in 100 ml of dichloromethane. After 2 hours' stirring, the reaction mixture is diluted with ethyl acetate. The organic phase is washed with water until pH=8, and the aqueous phase is then extracted with dichloromethane. After removal of the solvent by evaporation, the expected product is obtained.

Step b: 1-(N-tert-butyloxycarbonyl-pyrrolidin-3-ylmethyl)-6-nitroindole 100 g of maganese dioxide are added to a solution of 63.4 mmol (20 g) of the compound obtained in the preceding Step in 1 liter of toluene. The reaction mixture is heated at reflux for 2 hours. After cooling, the mineral salts are filtered off and the filtrate is concentrated. The residue is purified by chromatography on silica gel using a dichloromethane/methanol mixture (99/1) as eluant to obtain the expected product.

Step c: 6-Amino-1-(N-tert-butyloxycarbonyl-pyrrolidin-3-ylmethyl)indole

A solution of 28.1 mmol (9.7 g) of the compound described in the preceding Step in 350 ml of ethanol is stirred for 15 minutes in the presence of 4.7 g of palladium-on-carbon under hydrogen atmospheric pressure. The catalyst is removed by filtration, and the filtrate is concentrated to yield the expected compound.

Step d: 1-(N-tert-butyloxycarbonyl-pyrrolidin-3-ylmethyl)-6-([1,2,4]triazol-4-yl)indole A solution of 24.8 mmol of the compound described in the preceding Step, 24.6 mmol of N,N-dimethylformamide azine (obtained in accordance with the process described in J. Med. Chem., 1967, 1664) and 300 mg of para-toluenesulphonic acid in 100 ml of toluene is refluxed for 12 hours. After cooling, the organic phase is washed with water, and the aqueous phase is extracted with dichloromethane. The different organic phases are combined and concentrated, and the residue is purified by chromatography on silica gel using a dichloromethane/methanol/ammonia mixture (95/5/0.5) as eluant to yield the expected compound.

EXAMPLE 2

1-(Dimethylaminoethyl)-6-([1,2,4]triazol-4-yl)indole dihydrochloride

The expected product is obtained in accordance with the process described in Example 1, step d, starting with 6-amino-1-(2-dimethylaminoethyl)indole described in Application WO 95/32967. The corresponding dihydrochloride is obtained by the action of a titrated solution of hydrochloric acid in ethanol.

Melting point: 254–256° C.

EXAMPLE 3

1-(1-Benzylpiperid-4-yl)-6-([1,2,4]triazol-4-yl) indole dihydrochloride

Step a: 1-(1-Benzylpiperid-4-yl)-6-nitro-2,3-dihydroindole

The expected product is obtained in accordance with the process described in Example 1, Step a, replacing 1-(tert-butyloxycarbonyl)-3-formylpyrrolidine by N-benzyl-4-piperiodone.

Step b: 1-(1-Benzylpiperid-4-yl)-6-nitroindole

The expected product is obtained in accordance with the process described in Example 1, Step b, starting from the compound described in the preceding Step.

Step c: 6-Amino-1-(1-benzylpiperid-4-yl)indole

The expected product is obtained in accordance with the process in Example 1, Step c, starting from the compound described in the preceding Step.

Step d: 1-(1-Benzylpiperid-4-yl)-6-([1,2,4]triazol-4-yl) indole, dihydrochloride The expected product is obtained in accordance with the process described in Example 1, Step d, starting from the compound described in the preceding Step, followed by treatment of the base with a titrated solution of hydrochloric acid in ethanol.

EXAMPLE 4

1-[3-(4-Benzylpiperid-1-yl)propyl]-6-([1,2,4]triazol-4-yl)indole dihydrochloride Step a: 1-(3-Hydroxypropyl)-6-nitroindole 0.13 mol of potassium tert-butylate and 0.13 mol of 3-bromopropanol are added to a solution of 0.11 mol of 6-nitroindole in 400 ml of dimethylformamide. The reaction mixture is heated at 80° C. for 3 hours. After cooling, 300 ml of a 10% potassium carbonate solution are added, and the mixture is diluted with ethyl acetate. After decanting, the aqueous phase is extracted with dichloromethane, and the combined organic phases are then concentrated and purified by chromatography on silica gel to yield the expected product.

Step b: 1-(3-Bromopropyl)-6-nitroindole 0.12 mol of carbon tetrabromide, and then a solution of 0.12 mol of triphenylphosphine dissolved in 100 ml of dichloromethane, are added to a solution of 0.1 mol of the compound described in the preceding Step in 300 ml of dichloromethane. After 4 hours' stirring at room temperature, the reaction mixture is concentrated and purified by chromatography on silica gel to yield the expected compound.

Step c: 1-[3-(4-Benzylpiperid-1-yl)-propyl]-6-nitroindole 12 mmol of triethylamine and 12 mmol of 4-benzylpiperidine are added to a solution of 10 mmol of the compound described in the preceding Step in 30 ml of diethyl ketone. The reaction mixture is stirred for 6 hours at room temperature. After hydrolysis, the mixture is diluted with ethyl acetate and extracted. The organic phases are concentrated and purified by chromatography on silica gel to yield the expected compound.

Step d: 6-Amino-1-[3-(4-benzylpiperid-1-yl)propyl]-indole

The expected product is obtained in accordance with the process described in Example 1, Step c, starting from the compound described in the preceding Step.

Step e: 1-[3-(4-Benzylpiperid-1-yl)propyl]-6-([1,2,4]triazol-4-yl)indole dihydrochloride The expected product is obtained in accordance with the process described in Example 1, Step d, starting from the compound described in the preceding Step. The corresponding dihydrochloride is obtained by the action of a titrated solution of hydrochloric acid in ethanol.

EXAMPLE 5

1-{3-[4-(5-Methoxypyrimidin-4-yl)piperazin-1-yl]propyl}-6-([1,2,4]-triazol-4-yl)indole dihydrochloride Step a: 1-{3-[4-(5-Methoxypyrimidin-4-yl)piperazin-1-yl]propyl}-6-nitroindole The expected product is obtained in accordance with the process described in Example 4, Step c, replacing 4-benzylpiperidine by 4-(5-methoxypyrimidin-4-yl)piperazine.

Step b: 6-Amino-1-{3-[4-(5-Methoxypyrimidin-4-yl)piperazin-1-yl]propyl}-6-indole The expected product is obtained in accordance with the process described in Example 1, Step c, starting from the compound described in the preceding Step.

Step c: 1-{3-[4-(5-Methoxypyrimidin-4-yl)piperazin-1-yl]propyl}-6-([1,2,4]-triazol-4-yl)indole, dihydrochloride The expected product is obtained in accordance with the process described in Example 1, Step d, starting from the compound described in the preceding Step. The corresponding hydrochloride is obtained by the action of a titrated solution of hydrochloric acid in ethanol.

Melting point: 130–132° C.

EXAMPLE 6

1-(Dimethylaminoethyl)-6-([1,2,4]triazol-4-yl)indazole dihydrochloride

Step a: 1-(2-Dimethylaminoethyl)-6-nitroindazole 0.11 mol of potassium tert-butylate is added to a solution of 0.11 mol (20 g) of 6-nitroindazole in 400 ml of tetrahydrofuran. After total dissolution, a solution of 0.24 mol (27 g) of 2-chlorothyl-N,N-dimethylamine in 300 ml of toluene is added. The reaction medium is heated at reflux for 3 hours. After cooling, 300 ml of a 10% sodium carbonate solution are added. The mixture is diluted with ethyl acetate and decanted, and the aqueous phase is extracted with dichloromethane. After concentration of the organic phases, the residue is purified by chromatography on silica gel using a dichloromethane/methanol mixture (98/2) as eluant to yield the expected compound.

Step b: 6-Amino-1-(2-dimethylaminoethyl)indazole

The expected product is obtained in accordance with the process described in Example 1, Step c, starting from the compound described in the preceding Step.

Step c: 1-(2-Dimethylaminoethyl)-6-([1,2,4]triazol-4-yl)indazole dihydrochloride The expected product is obtained in accordance with the process described in Example 1, Step d, starting from the compound described in the preceding Step. The corresponding hydrochloride is obtained by the action of a titrated solution of hydrochloric acid in ethanol.

EXAMPLE 7

1-{3-[4-(5-Methoxypyrimidin-4-yl)piperazin-1-yl]propyl}-6-([1,2,4]-triazol-4-yl)indazole Step a: 1-(3-Hydroxypropyl)-6-nitroindazole The expected product is obtained in accordance with the process described in Example 4, Step a, replacing 6-nitroindole by 6-nitroindazole, and after separating the resulting positional isomers.

Step b: 1-(3-Bromopropyl)-6-nitroindazole

The expected product is obtained in accordance with the process described in Example 4, Step b, starting from the compound described in the preceding Step.

Step c: 1-{3-[4-(5-Methoxypyrimidin-4-yl)piperazin-1-yl]propyl}-6-nitroindazole

The expected product is obtained in accordance with the process described in Example 4, Step c, starting from the compound described in the preceding Step, replacing 4-benzylpiperidine by 4-(5-methoxypyrimidin-4-yl)piperazine.

Step d: 6-Amino-1-{3-[4-(5-methoxypyrimidin-4-yl)piperazin-1-yl]propyl}-indazole The expected product is obtained in accordance with the process described in Example 1, Step c, starting from the compound described in the preceding Step.

Step e: 1-{3-[4-(5-Methoxypyrimidin-4-yl)piperazin-1-yl]propyl}-6-([1,2,4]-triazol-4-yl)indazole The expected product is obtained in accordance with the process described in Example 1, Step d, starting from the compound described in the preceding Step.

EXAMPLE 8

1-(1-Methylpiperid-4-yl)-6-([1,2,4]triazol-4-yl)indole dihydrochloride

Step a: (1-Methylpiperid-4-yl)-6-nitro-2,3-dihydroindole

The expected product is obtained in accordance with the process described in Example 1, Step a, replacing 1-(tert-butyloxycarbonyl)-3-formylpyrrolidine by N-methyl-4-piperidone.

Step b: 1-(1-Methylpiperid-4-yl)-6-nitroindole

The expected product is obtained in accordance with the process described in Example 1, Step b, starting from the compound described in the preceding Step.

Step c: 6-Amino-1-(1-methylpiperid-4-yl)indole

The expected product is obtained in accordance with the process described in Example 1, Step c, starting from the compound described in the preceding Step.

Step d: 1-(1-Methylpiperid-4-yl)-6-([1,2,4]triazol-4-yl)indole dihydrochloride

The expected product is obtained in accordance with the process described in Example 1, Step d, starting from the compound described in the preceding Step.

The resulting base is then converted into a salt with a titrated solution of hydrochloric acid in ethanol.

Melting point: 195–198° C.

EXAMPLE 9

1-{3-[4-(2-Phenylethyl)piperazin-1-yl]propyl}-6-([1,2,4]triazol-4-yl)indole dihydrochloride Step a: 1-{3-[4-(2-Phenylethyl)piperazin-1-yl]propyl}-6-nitroindole The expected product is obtained in accordance with the process described in Example 4, Step c, replacing 4-benzylpiperidine by N-(2-phenylethyl)piperazine.

Step b: 6-Amino-1-{3-[4-(2-phenylethyl)piperazin-1-yl]propyl}indole

The expected product is obtained in accordance with the process described in Example 1, Step c, starting from the compound described in the preceding Step.

Step c: 1-{3-[4-(2-Phenylethyl)piperazin-1-yl]propyl}-6-([1,2,4]triazol-4-yl)-indole dihydrochloride The expected product is obtained in accordance with the process described in Example 1, Step d, starting from the compound described in the preceding Step.

The resulting base is then converted into a salt with a titrated solution of hydrochloric acid in ethanol.

Melting point: >270° C.

EXAMPLE 10

1-(Pyrrolidin-3-ylmethyl)-6-([1,2,4]triazol-4-yl)indole dihydrochloride

A solution of 30 mmol of the compound described in Example 1 in 300 ml of ethyl acetate is treated for 4 minutes at −10° C. with a stream of hydrochloric acid. The resulting precipitate is filtered off and rinsed with ether to yield the title product.

Melting point: 206° C.

EXAMPLE 11

1-[(N-Ethylpyrrolidin-3-yl)methyl]-6-([1,2,4]triazol-4-yl)indole dihydrochloride Step a: 1-(Pyrrolidin-3-ylmethyl)-6-nitroindole The expected product is obtained in accordance with the process described in Example 10, using the compound described in Example 1, Step b, as starting material.

Step b: 1-[(N-Ethylpyrrolidin-3-yl)methyl]-6-nitroindole

The expected product is obtained in accordance with the process described in Example 1, Step a, replacing 1-(tert-butyloxycarbonyl)-3-formylpyrrolidine by acetaldehyde, and using the compound described in the preceding Step as starting material.

Step c: 1-[(N-Ethylpyrrolidin-3-yl)methyl]-6-([1,2,4]triazol-4-yl)indole dihydrochloride The expected product is obtained in accordance with the process described in Example 1, Steps c and d, using the compound described in the preceding Step as starting material. The corresponding dihydrochloride is obtained by the action of a titrated solution of hydrochloric acid in ethanol.

EXAMPLE 12

1-{[N-Cyclohexylmethyl)pyrrolidin-3-yl]methyl}-6-([1,2,4]triazol-4-yl) indole dihydrochloride Step a: 1-{[N-Cyclohexylmethyl)pyrrolidin-3-yl]methyl}-6-nitroindole The expected product is obtained in accordance with the process described in Example 1, Step a, replacing 1-(tert-butyloxycarbonyl)-3-formylpyrrolidine by cyclohexanecarboxaldehyde, and using the compound described in Step a of Example 11 as starting material.

Step b: 1-{[N-Cyclohexylmethyl)pyrrolidin-3-yl]methyl}-6-([1,2,4]triazol-4-yl)indole dihydrochloride The expected product is obtained in accordance with the process described in Example 1, Steps c and d, using the compound described in the preceding Step as starting material. The corresponding dihydrochloride is obtained by the action of a titrated solution of hydrochloric acid in ethanol.

EXAMPLE 13

1-{[N-(2-Furylmethyl)pyrrolidin-3-yl]methyl}-6-([1,2,4]triazol-4-yl) indole dihydrochloride Step a: 1-{[N-(2-Furylmethyl)pyrrolidin-3-yl]methyl}-6-nitroindole The expected product is obtained in accordance with the process described in Example 1, Step a, replacing 1-(tert-butyloxycarbonyl)-3-formylpyrrolidine by 2-furfuraldehyde, and using the compound described in Step a of Example 11 as starting material.

Step b: 1-{[N-(2-Furylmethyl)pyrrolidin-3-yl]methyl}-6-([1,2,4]triazol-4-yl)indole dihydrochloride The expected product is obtained in accordance with the process described in Example 1, Steps c and d, using the compound described in the preceding Step as starting material. The corresponding dihydrochloride is obtained by the action of a titrated solution of hydrochloric acid in ethanol.

EXAMPLE 14

1-{[N-(2-Pyridylmethyl)pyrrolidin-3-yl]methyl}-6-([1,2,4]triazol-4-yl) indole dihydrochloride Step a: 6-Nitro-1-{[N-(2-pyridylmethyl)pyrrolidin-3-yl]methyl}indole The expected product is obtained in accordance with the process described in Example 1, Step a, replacing 1-(tert-butyloxycarbonyl)-3-formylpyrrolidine by 2-pyridinecarboxaldehyde, and using the compound described in Step a of Example 11 as starting material.

Step b: 1-{[N-(2-Pyridylmethyl)pyrrolidin-3-yl]methyl}-6-([1,2,4]triazol-4-yl)indole dihydrochloride The expected product is obtained in accordance with the process described in Example 1, Steps c and d, using the compound described in the preceding Step as starting material. The corresponding dihydrochloride is obtained by the action of a titrated solution of hydrochloric acid in ethanol.

EXAMPLE 15

1-(4-Piperidyl)-6-([1,2,4]triazol-4-yl)indole dihydrochloride

Step a: 6-Nitro-1-(1-carbethoxy-4-piperidyl)indole

The expected product is obtained in accordance with the process described in Example 1, Step a, replacing 1-(tert-butyloxycarbonyl)-3-formylpyrrolidine by N-carbethoxy-4-piperidone.

Step b: 1-(1-Carbethoxy-4-piperidyl)6-([1,2,4]triazol-4-yl)indole

The expected product is obtained in accordance with the process described in Example 1, Steps c and d, using the compound described in the preceding Step as starting material.

Step c: 1-(4-Piperidyl)-6-([1,2,4]triazol-4-yl)indole dihydrochloride

The expected product is obtained in accordance with the process described in Example 10, using the compound described in the preceding Step as starting material and an aqueous solution of chlorhydric acid.

EXAMPLE 16

1-[1-(2-Pyridylmethyl)piperid-4-yl]-6-([1,2,4]
triazol-4-yl)indole dihydrochloride Step a: 6-Nitro-1-[1-(2-pyridylmethyl)piperid-4-yl]indole The expected product is obtained in accordance with the process described in Example 1, Step a, replacing 1-(tert-butyloxycarbonyl)-3-formylpyrrolidine by 2-pyridinecarboxaldehyde, and using the compound described in Example 15, step a, as starting material.

Step b: 1-[1-(2-Pyridylmethyl)piperid-4-yl]6-([1,2,4]triazol-4-yl)indole dihydrochloride The expected product is obtained in accordance with the process described in Example 1, Steps c and d, using the compound described in the preceding Step as starting material. The corresponding dihydrochloride is obtained by the action of a titrated solution of hydrochloric acid in ethanol.

EXAMPLE 17

1-[1-(2-(2-Furylmethyl)piperid-4-yl]-6-([1,2,4]
triazol-4-yl)indole dihydrochloride Step a: 1-[1-(2-(2-Furylmethyl)piperid-4-yl]-6-nitroindole The expected product is obtained in accordance with the process described in Example 1, Step a, replacing 1-(tert-butyloxycarbonyl)-3-formylpyrrolidine by 2-furfuraldehyde, and using the compound described in Example 15, step a, as starting material.

Step b: 1-[1-(2-(2-Furylmethyl)piperid-4-yl]-6-([1,2,4]triazol-4-yl)indole dihydrochloride The expected product is obtained in accordance with the process described in Example 1, Steps c and d, using the compound described in the preceding Step as starting material. The corresponding dihydrochloride is obtained by the action of a titrated solution of hydrochloric acid in ethanol.

EXAMPLE 18

1-[1-(3-Phenylpropyl)piperid-4-yl]-6-([1,2,4]triazol-
4-yl)indole dihydrochloride Step a: 6-Nitro-1-[1-(3-phenyl-2-propenyl)piperid-4-yl]indole The expected product is obtained in accordance with the process described in Example 1, Step a, replacing 1-(tert-butyloxycarbonyl)-3-formylpyrrolidine by cinnamic aldehyde, and using the compound described in Example 15, step a, as starting material.

Step b: 1-[1-(3-Phenylpropyl)piperid-4-yl]-6-([1,2,4]triazol-4-yl)indole dihydrochloride The expected product is obtained in accordance with the process described in Example 1, Steps c and d, using the compound described in the preceding Step as starting material. The corresponding dihydrochloride is obtained by the action of a titrated solution of hydrochloric acid in ethanol.

EXAMPLE 19

1-[1-(Cyclohexylmethyl)piperid-4-yl]-6-([1,2,4]
triazol-4-yl)indole dihydrochloride Step a: 1-[1-(Cyclohexylmethyl)piperid-4-yl]-6-nitroindole The expected product is obtained in accordance with the process described in Example 1, Step a, replacing 1-(tert-butyloxycarbonyl)-3-formylpyrrolidine by cyclohexanecarboxaldehyde, using the compound described in Example 15, step a, as starting material.

Step b: 1-[1-(Cyclohexylmethyl)piperid-4-yl]-6-([1,2,4]triazol-4-yl)indole dihydrochloride The expected product is obtained in accordance with the process described in Example 1, Steps c and d, using the compound described in the preceding Step as starting material. The corresponding dihydrochloride is obtained by the action of a titrated solution of hydrochloric acid in ethanol.

EXAMPLE 20

1-[3-(2-Methylpiperid-1-yl)propyl]-6-([1,2,4]triazol-
4-yl)indole dihydrochloride The expected product is obtained in accordance with the process described in Example 4, replacing 4-benzylpiperidine by 2-methylpiperidine in Step c.

EXAMPLE 21

1-[3-(4-Methylpiperid-1-yl)propyl]-6-([1,2,4]triazol-
4-yl)indole dihydrochloride The expected product is obtained in accordance with the process described in Example 4, replacing 4-benzylpiperidine by 4-methylpiperidine in Step c.

EXAMPLE 22

1-[3-(2,6-Dimethylpiperid-1-yl)propyl]-6-([1,2,4]
triazol-4-yl)indole dihydrochloride The expected product is obtained in accordance with the process described in Example 4, replacing 4-benzylpiperidine by 2,6-dimethylpiperidine in Step c.

EXAMPLE 23

1-[3-(3,5-Dimethylpiperid-1-yl)propyl]-6-([1,2,4]
triazol-4-yl)-indole dihydrochloride The expected product is obtained in accordance with the process described in Example 4, replacing 4-benzylpiperidine by 3,5-dimethylpiperidine in Step c.

EXAMPLE 24

1-[2-(Benzylamino)ethyl]-6-([1,2,4]triazol-4-yl)
indole dihydrochloride

The expected product is obtained in accordance with the process described in Example 4, replacing 3-bromopropanol by 2-bromoethanol in Step a and replacing 4-benzylpiperidine by benzylamine in Step c.

EXAMPLE 25

1-[3-(Benzylamino)propyl]-6-([1,2,4]triazol-4-yl)
indole dihydrochloride

The expected product is obtained in accordance with the process described in Example 4, replacing 4-benzylpiperidine by benzylamine in Step c.

EXAMPLE 26

1-[3-(Phenylamino)propyl]-6-([1,2,4]triazol-4-yl)
indole dihydrochloride

The expected product is obtained in accordance with the process described in Example 4, replacing 4-benzylpiperidine by aniline in Step c.

EXAMPLE 27

1-[3-(Cyclohexylamino)propyl]-6-([1,2,4]triazol-4-
yl)indole dihydrochloride

The expected product is obtained in accordance with the process described in Example 4, replacing 4-benzylpiperidine by cyclohexylamine in Step c.

EXAMPLE 28

1-[3-(1-Piperazinyl)propyl]-6-([1,2,4]triazol-4-yl)
indole dihydrochloride

The expected product is obtained in accordance with the process described in Example 4, replacing 4-benzylpiperidine by piperazine in large excess in Step c.

EXAMPLE 29

1-[3-(4-Phenylpiperazin-1-yl)propyl]-6-([1,2,4]
triazol-4-yl)indole dihydrochloride The expected product is obtained in accordance with the process described in Example 4, replacing 4-benzylpiperidine by 4-phenylpiperazine in Step c.

EXAMPLE 30

1-{3-[4-(2-Pyridyl)piperazin-1-yl]propyl}-6-([1,2,4]
triazol-4-yl)-indole dihydrochloride The expected product is obtained in accordance with the process described in Example 4, replacing 4-benzylpiperidine by 1-(2-pyridyl)piperazine in Step c.

EXAMPLE 31

1-[3-(4-Methylpiperazin-1-yl)propyl]-6-([1,2,4]
triazol-4-yl)indole dihydrochloride The expected product is obtained in accordance with the process described in Example 4, replacing 4-benzylpiperidine by 1-methylpiperazine in Step c.

EXAMPLE 32

1-[3-(4-Cyclohexylpiperazin-1-yl)propyl]-6-([1,2,4]
triazol-4-yl)-indole dihydrochloride The expected product is obtained in accordance with the process described in Example 4, replacing 4-benzylpiperidine by cyclohexylpiperazine in Step c.

EXAMPLE 33

1-{3-[4-(2-Pyridylmethyl)piperazin-1-yl]propyl}-6-
([1,2,4]triazol-4-yl)indole dihydrochloride Step a: 6-Nitro-1-{3-[4-(2-pyridylmethyl)piperazin-
1-yl]propyl}indole The expected product is obtained in accordance with the process described in Example 1, Step a, replacing 1-(tert-butyloxycarbonyl)-3-formylpyrrolidine by 2-pyridinecarboxaldehyde, and using 6-nitro-1-[(1-piperazinyl)propyl]indole (isolated in the course of the process for the preparation of the compound described in Example 28) as starting material.

Step b: 1-{3-[4-(2-Pyridylmethyl)piperazin-1-yl]
propyl}-6-([1,2,4]triazol-4yl)indole dihydrochloride The expected product is obtained in accordance with the process described in Example 1, Steps c and d, using the compound described in the preceding Step as starting material. The corresponding dihydrochloride is obtained by the action of a titrated solution of hydrochloric acid in ethanol.

EXAMPLE 34

1-{3-[4-(3-Trifluoromethylphenyl)piperazin-1-yl)
propyl}-6-([1,2,4]-triazol-4-yl)indole
dihydrochloride The expected product is obtained in accordance with the process described in Example 4, replacing 4-benzylpiperidine by 1-(3-trifluoromethylphenyl)piperazine in Step c.

EXAMPLE 35

1-[N-(tert-butyloxycarbonylpyrrolidin-3-yl)methyl]-
6-([1,2,4]-triazol-4-yl)indazole The expected product is obtained in accordance with the process described in Example 1, Steps a, c and d, replacing 6-nitroindoline by 6-nitroindazole.

EXAMPLE 36

1-(3-Pyrrolidinylmethyl)-6-([1,2,4]triazol-4-yl)
indazole dihydrochloride

The expected product is obtained in accordance with the process described in Example 10, using the compound described in Example 35 as starting material.

EXAMPLE 37

1-{[N-(Cyclohexylmethyl)pyrrolidin-3-yl]methyl}-
6-([1,2,4]triazol-4-yl)indazole dihydrochloride Step a: 6-Nitro-1-(3-pyrrolidinylmethyl)indazole The expected product is obtained in accordance with the process described in Example 10, using as starting material 1-[N-(tert-butyloxycarbonylpyrrolidin-3-yl)methyl]-6-nitroindazole, isolated in the course of the process for the preparation of the compound described in Example 35.

Step b: 1-{[N-(Cyclohexylmethyl)pyrrolidin-3-yl]
methyl}-6-nitroindazole

The expected product is obtained in accordance with the process described in Example 1, Step a, replacing 1-(tert-butyloxycarbonyl)-3-formylpyrrolidine by cyclohexanecarboxaldehyde, and using the compound described in the preceding Step as starting material.

Step c: 1-{[N-(Cyclohexylmethyl)pyrrolidin-3-yl]
methyl}-6-([1,2,4]triazol-4-yl)-indazole
dihydrochloride The expected product is obtained in accordance with the process described in Example 1, Steps c and d, using the compound described in the preceding Step as starting material.

The corresponding dihydrochloride is obtained by the action of a titrated solution of hydrochloric acid in ethanol.

EXAMPLE 38

1-{[N-(2-Pyridylmethyl)pyrrolidin-3-yl]methyl}-6-
([1,2,4]triazol-4-yl)indazole dihydrochloride Step a: 6-Nitro-1-{[N-(2-pyridylmethyl)pyrrolidin-
3-yl]methyl}indazole The expected product is obtained in accordance with the process described in Example 1, Step a, replacing 1-(tert-butyloxycarbonyl)-3-formylpyrrolidine by 2-pyridinecarboxaldehyde, and using the compound described in Example 37, Step a, as starting material.

Step b: 1-{[N-(2-Pyridylmethyl)pyrrolidin-3-yl]
methyl}-6-([1,2,4]triazol-4-yl)indazole,
dihydrochloride The expected product is obtained in accordance with the process described in Example 1, Steps c and d, using the compound described in preceding Step as starting material. The corresponding dihydrochloride is obtained by the action of a titrated solution of hydrochloric acid ethanol.

EXAMPLE 39

1-(4-Piperidyl)-6-([1,2,4]triazol-4-yl)indazole dihydrochloride

Step a: 6-Nitro-1-(1-carbethoxy-4-piperidyl) indazole

The expected product is obtained in accordance with the process described in Example 1, Step a, replacing 1-(tert-butyloxycarbonyl)-3-formylpyrrolidine by N-carbethoxy-4-piperidone, and using 6-nitroindazole as starting material.

Step b: 1-(1-Carbethoxy-4-piperidyl)-6-([1,2,4] triazol-4-yl)indazole

The expected product is obtained in accordance with the process described in Example 1, Steps c and d, using the compound described in the preceding Step as starting material.

Step c: 1-(4-Piperidyl)-6-([1,2,4]triazol-4-yl) indazole dihydrochloride

The expected product is obtained in accordance with the process described in Example 10, using the compound described in the preceding Step as starting material and an aqueous solution of chlorhydric acid.

EXAMPLE 40

1-(N-Benzylpiperid-4-yl)-6-([1,2,4]triazol-4-yl) indazole dihydrochloride

Step a: 1-(N-Benzylpiperid-4-yl)-6-nitroindazole

The expected product is obtained in accordance with the process described in Example 1, Step a, replacing 1-(tert-butyloxycarbonyl)-3-formylpyrrolidine by N-benzyl-4-piperidone, and using 6-nitroindazole as starting material.

Step b: 1-(N-Benzylpiperid-4-yl)-6-([1,2,4]triazol-4-yl)indazole dihydrochloride The expected product is obtained in accordance with the process described in Example 1, Steps c and d, using the compound described in the preceding Step as starting material.

The corresponding dihydrochloride is obtained by the action of a titrated solution of hydrochloric acid in ethanol.

EXAMPLE 41

1-[N-(2-Furylmethyl)piperid-4-yl]-6-([1,2,4]triazol-4-yl)indazole dihydrochloride Step a: 1-[N-(2-Furylmethyl)piperid-4-yl]-6-nitroindazole The expected product is obtained in accordance with the process described in Example 1, Step a, replacing 1-(tert-butyloxycarbonyl)-3-formylpyrrolidine by 2-furfuraldehyde, and using the compound described in Example 39, Step a, as starting material.

Step b: 1-[N-(2-Furylmethyl)piperid-4-yl]-6-([1,2,4] triazol-4-yl)indazole dihydrochloride The expected product is obtained in accordance with the process described in Example 1, Steps c and d, using the compound described in the preceding Step as starting material.

The corresponding dihydrochloride is obtained by the action of a titrated solution of hydrochloric acid in ethanol.

EXAMPLE 42

1-(N-Methylpiperid-4-yl)-6-([1,2,4]triazol-4-yl) indazole dihydrochloride

Step a: 1-(N-Methylpiperid-4-yl)-6-nitroindazole

The expected product is obtained in accordance with the process described in Example 1, Step a, replacing 1-(tert-butyloxycarbonyl)-3-formylpyrrolidine by N-methyl-4-piperidone.

Step b: 1-(N-Methylpiperid-4-yl)-6-([1,2,4]triazol-4-yl)indazole dihydrochloride The expected product is obtained in accordance with the process described in Example 1, Steps c and d, using the compound described in the preceding Step as starting material.

The corresponding dihydrochloride is obtained by the action of a titrated solution of hydrochloric acid in ethanol.

EXAMPLE 43

1-[3-(Benzylamino)propyl]-6-([1,2,4]triazol-4-yl) indazole dihydrochloride

The expected product is obtained in accordance with the process described in Example 4, using 6-nitroindazole as starting material, and replacing 4-benzylpiperidine by benzylamine in Step c, and using hydrazine in the presence of nickel as reductive agent, in step d.

EXAMPLE 44

1-[3-(1-Piperazinyl)propyl]-6-([1,2,4]triazol-4-yl) indazole dihydrochloride

The expected product is obtained in accordance with the process described in Example 4, using 6-nitroindazole as starting material, and replacing 4-benzylpiperidine by piperazine in large excess in Step c.

EXAMPLE 45

1-{3-[4-(2-Phenylethyl)piperazin-1-yl]propyl}-6-([1, 2,4]triazol-4-yl)indazole dihydrochloride The expected product is obtained in accordance with the process described in Example 4, using 6-nitroindazole as starting material, and replacing 4-benzylpiperidine by 4-(2-phenylethyl)piperazine in Step c.

EXAMPLE 46

1-{3-[4-(3-Trifluoromethylphenyl)piperazin-1-yl] propyl}-6-([1,2,4]-triazol-4-yl)indazole dihydrochloride The expected product is obtained in accordance with the process described in Example 4, using 6-nitroindazole as starting material, and replacing 4-benzylpiperidine by 1-(3-trifluoromethylphenyl)piperazine in Step c.

EXAMPLE 47

1-[3-(4-Methylpiperazin-1-yl)propyl]-6-([1,2,4] triazol-4-yl)indazole dihydrochloride The expected product is obtained in accordance with the process described in Example 4, using 6-nitroindazole as starting material, and replacing 4-benzylpiperidine by 1-methylpiperazine in Step c.

EXAMPLE 48

1-[3-(4-Cyclohexylpiperazin-1-yl)propyl]-6-([1,2,4]triazol-4-yl)indazole dihydrochloride The expected product is obtained in accordance with the process described in Example 4, using 6-nitroindazole as starting material, and replacing 4-benzylpiperidine by cyclohexylpiperazine in Step c.

The compounds of Examples 49 to 56 are obtained in accordance with the process described in the preceding Examples, using 3-methyl-6-nitroindole as starting material.

EXAMPLE 49

1-(Dimethylaminoethyl)-3-methyl-6-([1,2,4]triazol-4-yl)indole dihydrochloride

EXAMPLE 50

3-Methyl-1-[(pyrrolidin-3-yl)methyl]-6-([1,2,4]triazol-4-yl)indole dihydrochloride

EXAMPLE 51

3-Methyl-1-(1-methylpiperid-4-yl)-6-([1,2,4]triazol-4-yl)indole dihydrochloride

EXAMPLE 52

1-(1-Benzylpiperid-4-yl)-3-methyl-6-([1,2,4]triazol-4-yl)indole dihydrochloride

EXAMPLE 53

1-[3-(4-Benzylpiperid-1-yl)propyl]-3-methyl-6-([1,2,4]triazol-4-yl)indole dihydrochloride

EXAMPLE 54

1-{3-[4-(5-Methoxypyrimidin-4-yl)piperazin-1-yl]propyl}-3-methyl-6-([1,2,4]triazol-4-yl)indole dihydrochloride

EXAMPLE 55

3-Methyl-1-{3-[4-(2-phenylethyl)piperazin-1-yl]propyl}-6-([1,2,4]triazol-4-yl)indole dihydrochloride

EXAMPLE 56

1-[3-(4-Methylpiperazine-1-yl)propyl]-3-methyl-6-([1,2,4]triazol-4-yl)indole dihydrochloride

EXAMPLE 57

1-(1-Benzylpiperid-4-yl)-6-([1,2,4]triazol-4-ylmethyl)indole dihydrochloride

Step a: 1-(1-Benzylpiperid-4-yl)-6-hydroxymethylindole

The expected product is obtained in accordance with the process described in Example 1, Step a, replacing 1-(tert-butyloxycarbonyl)-3-formylpyrrolidine by N-benzylpiperidone and using 6-hydroxymethylindole (prepared from the corresponding carboxylic acid) as starting material.

Step b: [1-(1-Benzylpiperid-4-yl)-6-indolyl]methyl methanesulfonate 14.5 mmol (2 ml) of triethylamine and, dropwise, 14.5 mmol (1.12 ml) of mesylchloride are added to a solution of 12 mmol (3.85 g) of the compound described in the preceding Step in 50 ml of dichloromethane.

The reaction mixture is stirred for 5 hours at room temperature. After hydrolysis and extraction with dichloromethane, the organic phase is washed by a 0.1 N aqueous hydrochloric acid solution, dried and concentrate to yield the expected compound.

Step c: 6-(Azidomethyl)-1-(1-benzylpiperid-4-yl)indole 21.6 mmol of sodium azide are added to a solution of 10.8 mmol of the compound described in the preceding Step in 20 ml of dimethylsulfoxyde. The reaction mixture is stirred for 1 hour at room temperature. After hydrolysis, the reaction medium is extracted with ethylacetate, and the organic phase is dried and concentrate to yield the expected product.

Step d: 6-Aminomethyl-1-(1-benzylpiperid-4-yl)indole

The expected product is obtained in accordance with the process described in Example 1, Step c, using the compound described in the preceding Step as starting material.

Step e: 1-(1-Benzylpiperid-4-yl)-6-([1,2,4]triazol-4-ylmethyl)indole dihydrochloride The expected product is obtained in accordance with the process described in Example 1, Step d, using the compound described in the preceding Step as starting material.

Melting point: >270° C. (dec.)

In the same manner compounds of example 58 to 65 are obtained.

EXAMPLE 58

1-(1-Methylpiperid-4-yl)-6-([1,2,4]triazol-4-ylmethyl)indole dihydrochloride

EXAMPLE 59

1-[3-(4-benzylpiperid-1-yl)propyl]-6-([1,2,4]triazol-4-yl-methyl)indole dihydrochloride

EXAMPLE 60

1-{3-[4-(2-Phenylethyl)piperazin-1-yl]propyl}-6-([1,2,4]triazol-4-ylmethyl)indole dihydrochloride

EXAMPLE 61

1-{3-[4-(5-Methoxypyrimidin-4-yl)piperazin-1-yl]propyl}-6-([1,2,4]triazol-4-ylmethyl)indole dihydrochloride

EXAMPLE 62

1-{[N-(2-Pyridylmethyl)pyrrolidin-3-yl]methyl}-6-([1,2,4]triazol-4-ylmethyl)indole dihydrochloride

EXAMPLE 63

1-(Dimethylaminoethyl)-6-([1,2,4]triazol-4-ylmethyl)indazole dihydrochloride

EXAMPLE 64

1-{3-[4-(2-Phenylethyl)piperazin-1-yl]propyl}-6-([1,2,4]triazol-4-ylmethyl)indazole dihydrochloride

EXAMPLE 65

1-{3-[4-(5-Methoxypyrimid-4-yl)piperazin-1-yl]propyl}-6-([1,2,4]triazol-4-ylmethyl)indazole dihydrochloride The compounds of Examples 66 to 79 are obtained using processes similar to those described in the preceding Examples, replacing the 6-nitroindole and 6-nitroindazole starting materials by 5-nitroindole and 5-nitroindazole.

EXAMPLE 66

1-(Dimethylaminoethyl)-5-([1,2,4]triazol-4-yl)indole dihydrochloride

EXAMPLE 67

1-(Pyrrolidin-3-ylmethyl)-5-([1,2,4]triazol-4-yl)indole dihydrochloride

EXAMPLE 68

1-(1-Methylpiperid-4-yl)-5-([1,2,4]triazol-4-yl)indole dihydrochloride

EXAMPLE 69

1-[1-(2-Pyridylmethyl)piperid-4-yl]-5-([1,2,4]triazol-4-yl)indole dihydrochloride

EXAMPLE 70

1-(1-Benzylpiperid-4-yl)-5-([1,2,4]triazol-4-yl)indole dihydrochloride

EXAMPLE 71

1-[3-(4-Benzylpiperid-1-yl)propyl]-5-([1,2,4]triazol-4-yl)indole dihydrochloride

EXAMPLE 72

1-{3-[4-(5-Methoxypyrimidin-4-yl)piperazin-1-yl]propyl}-5-([1,2,4]triazol-4-yl)indole dihydrochloride

EXAMPLE 73

1-{3-[4-(2-Phenylethyl)piperazin-1-yl]propyl}-5-([1,2,4]triazol-4-yl)indole dihydrochloride

EXAMPLE 74

1-{3-[4-(3-Trifluoromethylphenyl)piperazin-1-yl]propyl}-5-([1,2,4]triazol-4-yl)indole dihydrochloride

EXAMPLE 75

1-(Dimethylaminoethyl)-5-([1,2,4]triazol-4-yl)indazole dihydrochloride

EXAMPLE 76

1-(1-Methylpiperid-4-yl)-5-([1,2,4]triazol-4-yl)indazole dihydrochloride

EXAMPLE 77

1-[3-(4-Benzylpiperid-1-yl)propyl]-5-([1,2,4]triazol-4-yl)indazole dihydrochloride

EXAMPLE 78

1-{3-[4-(2-Phenylethyl)piperazin-1-yl]propyl}-5-([1,2,4]triazol-4-yl)indazole dihydrochloride

EXAMPLE 79

1-{3-[4-(5-Methoxypyrimidin-4-yl)piperazin-1-yl]propyl}-5-([1,2,4]triazol-4-yl)indazole dihydrochloride The compounds of Examples 80 to 85 are obtained in the same manner, using 4-nitroindole as starting material.

EXAMPLE 80

1-(Dimethylaminoethyl)-4-([1,2,4]triazol-4-yl)indole dihydrochloride

EXAMPLE 81

1-(Pyrrolidin-3-ylmethyl)-4-([1,2,4]triazol-4-yl)indole dihydrochloride

EXAMPLE 82

1-(1-Methylpiperid-4-yl)-4-([1,2,4]triazol-4-yl)indole dihydrochloride

EXAMPLE 83

1-[3-(4-Benzylpiperid-1-yl)propyl]-4-([1,2,4]triazol-4-yl)indole dihydrochloride

EXAMPLE 84

1-{3-[4-(5-Methoxypyrimidin-4-yl)piperazin-1-yl]propyl}-4-([1,2,4]triazol-4-yl)indole dihydrochloride

EXAMPLE 85

1-{3-[4-(2-Phenylethyl)piperazin-1-yl]propyl}-4-([1,2,4]triazol-4-yl)indole dihydrochloride The compounds of Examples 86 to 90 are obtained in the same manner, using 7-nitroindazole as starting material.

EXAMPLE 86

1-(Dimethylaminoethyl)-7-([1,2,4]triazol-4-yl)indazole dihydrochloride

EXAMPLE 87

1-(1-Methylpiperid-4-yl)-7-([1,2,4]triazol-4-yl)indazole dihydrochloride

EXAMPLE 88

1-[3-(4-Benzylpiperid-1-yl)propyl]-7-([1,2,4]triazol-4-yl)indazole dihydrochloride

EXAMPLE 89

1-{3-[4-(2-Phenylethyl)piperazin-1-yl]propyl}-7-([1,2,4]triazol-4-yl)indazole dihydrochloride

EXAMPLE 90

1-{3-[4-(5-Methoxypyrimidin-4-yl)piperazin-1-yl]propyl}-7-([1,2,4]triazol-4-yl)indazole dihydrochloride

PHARMACOLOGICAL STUDY OF THE COMPOUNDS OF THE INVENTION

Example A

Contraction of the Saphenous Vein

The test are carried out on saphenous veins of dogs (10–25 kg) or of rabbits (2–3 kg) which have ben anaesthetised with pentobarbital (30 mg/kg i.v.). The saphenous veins are removed quickly and cut into rings. The rings are mounted between two hooks in vessels maintained at 37° C. containing physiological saline (composition in mM:NaCl 118.3; KCl 4.7; CaCl$_2$ 2.5; MgSO$_4$ 1.2; KH$_2$PO$_4$ 1.2; NaHCO$_3$ 25.0; Ca-EDTA 0.026 and glucose 11.1).

A mixture of 95% O$_2$—5% CO$_2$ is bubbled through the physiological saline solution. The lower hook consists of the fixed point whilst the upper hook is connected to an isometric force sensor. The tissues are subjected to a base tension of 1.5 grammes (dog) and of 1 gramme (rabbit). The test pharmacological substances are prepared immediately prior to use; they are solubilised in water or in dimethyl sulphoxide.

After being mount, the preparations are left to rest for 60 minutes, rinsing operations being carried out every 30 minutes. The organ is then placed in the presence of phenoxybenzamine (5×10$^{-8}$M) for 20 minutes. That agent is eliminated by a number of successive washing operations over the course of 45 minutes. After readjustment of the base tension, contraction is brought about by KCl (100 mM). After washing and return to the base line, contraction is induced by 5-hydroxytryptamine (10$^{-5}$M).

After washing and return to the base line, a dose/response curve for the pharmacological substances is produced by the addition of cumulative doses (10$^{-9}$ to 10$^{-4}$M).

The test enables the 50% effective concentration (EC$_{50}$) of the compounds of the invention to be determined.

The EC$_{50}$ is calculated in the following manner: the tension values are first converted into percentages relative to the maximum effect induced by KCl. The effective concentration 50% (ED$_{50}$) is determined by non-linear regression according to the model of the law of mass action of Michaelis-Menten.

Results

The compounds of Examples 5 and 6 contract the saphenous vein of rabbits at EC$_{50}$ values of 0.30 μM and 0.12 μM, respectively, and with maximum responses of 75% and 87%, respectively.

On the saphenous vein of dogs, the EC$_{50}$ of the compound of Example 6 is 0.17 μM and the maximum response is 47%. The compound of Example 5 brings about a maximum contraction of 6% at a concentration of 100 μM.

Example B

Pharmaceutical Compositions

Formulation for the preparation of 1000 tablets each comprising 10 mg of active ingredient:

Compound of Example 5 . . . 10 g

Hydroxypropyl cellulose . . . 2 g

Wheat starch . . . 10 g

Lactose . . . 100 g

Magnesium stearate . . . 3 g

Talc . . . 3 g

We claim:

1. A compound selected from those of formula (I):

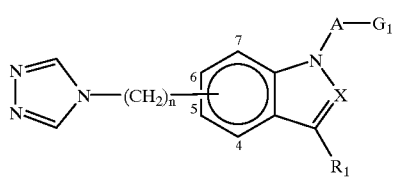

wherein:

n is 0 or 1,

A represents a σ bond or linear or branched (C$_1$–C$_8$) alkylene, or linear or branched (C$_1$–C$_8$)alkenylene, X represents nitrogen or C—R$_2$ wherein R$_2$ represents hydrogen, or linear or branched (C$_1$–C$_6$)alkyl, R$_1$ represents hydrogen, or linear or branched (C$_1$–C$_6$) alkyl, G$_1$ represents

wherein:

R$_3$ and R$_4$ each independently of the other represent hydrogen, linear or branched (C$_1$–C$_6$)alkyl, (C$_3$–C$_7$) cycloalkyl, (C$_3$–C$_7$)cycloalkyl-(C$_1$–C$_6$)-alkyl in which the alkyl is linear or branched, optionally substituted aryl-(C$_1$–C$_6$)alkyl in which the alkyl is linear or branched, or optionally substituted aryl, or together with the nitrogen atom that carries them, R$_3$ and R$_4$ form a group:

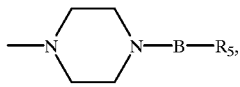

wherein B represents a σ bond or linear or branched (C$_1$–C$_6$) alkylene, and R$_5$ represents hydrogen, linear or branched (C$_1$–C$_6$)alkyl, (C$_3$–C$_6$)-cycloalkyl, optionally substituted aryl, optionally substituted aryl-(C$_1$–C$_6$)alkyl in which the alkyl is linear or branched, optionally substituted heteroaryl, or optionally substituted heteroaryl-(C$_1$–C$_6$)alkyl in which the alkyl is linear or branched, their enantiomers and diastereoisomers, and addition salts thereof with a pharmaceutically acceptable acid or base, it being understood that:

"aryl" is understood to mean a group selected from phenyl and naphthyl,

"heteroaryl" is understood to mean a group selected from furyl, thienyl, pyridyl, pyrrolyl, imidazolyl, tetrazolyl, pyrazinyl and pyrimidinyl, and the term optionally substituted applied to the terms "phenyl", "benzyl", "aryl", "arylalkyl", "heteroaryl" and "heteroarylalkyl" means that the groups in question may be substituted by one or more halogen, linear or branched (C$_1$–C$_6$)alkyl, linear or branched (C$_1$–C$_6$)alkoxy, hydroxy, and/or linear or branched (C$_1$–C$_6$)trihaloalkyl.

2. A compound of claim 1 wherein the triazolyl or triazolylmethyl is attached to the 6-position of the indole or indazole, their enantiomers and diastereoisomers, and addition salts thereof with a pharmaceutically-acceptable acid or base.

3. A compound of claim 1 wherein the triazolyl or triazolylmethyl group is attached to the 5-position of the indole or indazole group, their enantiomers and diastereoisomers, and addition salts thereof with a pharmaceutically-acceptable acid or base.

4. A compound of claim 1 wherein n=0, their enantiomers and diastereoisomers, and addition salts thereof with a pharmaceutically-acceptable acid or base.

5. A compound of claim 1 wherein X represent C—R$_2$ wherein R$_2$ represents hydrogen or linear or branched (C$_1$–C$_6$)alkyl, their enantiomers and diastereoisomers, and addition salts thereof with a pharmaceutically-acceptable acid or base.

6. A compound of claim 2 wherein X represents nitrogen, their enantiomers and diastereoisomers, and addition salts thereof with a pharmaceutically-acceptable acid or base.

7. A compound of claim 1 wherein A represents a σ bond or linear or branched ($C_1$–$C_6$)alkylene, and $G_1$ represents

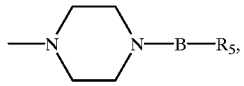

wherein B represent a σ bond or linear or branched ($C_1$–$C_6$) alkylene, and $R_5$ represents hydrogen, linear or branched ($C_1$–$C_6$)alkyl, ($C_3$–$C_6$)cycloalkyl, optionally substituted aryl, optionally substituted aryl-($C_1$–$C_6$)alkyl in which the alkyl is linear or branched, optionally substituted heteroaryl, or optionally substituted heteroaryl-($C_1$–$C_6$)alkyl in which the alkyl is linear or branched, their enantiomers and diastereoisomers, and addition salts thereof with a pharmaceutically-acceptable acid or base.

8. A compound of claim 1 wherein A represent linear or branched ($C_1$–$C_6$)alkylene and $G_1$ represents

wherein $R_3$ and $R_4$ each independently of the other represents hydrogen, linear or branched ($C_1$–$C_6$)alkyl, ($C_3$–$C_7$) cycloalkyl, ($C_3$–$C_7$)cycloalkyl-($C_1$–$C_6$)alkyl in which the alkyl is linear or branched, optionally substituted aryl-($C_1$–$C_6$)alkyl in which the alkyl is linear or branched, or optionally substituted aryl, their enantiomers and diastereoisomers, and addition salts thereof with a pharmaceutically-acceptable acid or base.

9. A compound of claim 1 wherein the triazolyl or triazolylmethyl is attached to the 6-position of the indole or indazole, X represent —CH— or nitrogen, $R_1$ represent hydrogen, A represents a σ bond or linear or branched ($C_1$–$C_6$)alkylene and $G_1$ represents 1-piperazinyl optionally substituted on the nitrogen in the 4-position by linear or branched ($C_1$–$C_6$)alkyl, optionally substituted aryl, optionally substituted aryl-($C_1$–$C_6$)alkyl in which the alkyl is linear or branched, optionally substituted heteroaryl, or optionally substituted heteroaryl-($C_1$–$C_6$)-alkyl in which the alkyl is linear or branched, or alternatively A represents linear or branched ($C_1$–$C_6$)alkylene and $G_1$ represents

wherein $R_3$ and $R_4$ each independently of the other represent hydrogen or linear or branched ($C_1$–$C_6$)alkyl, their enantiomers and diastereoisomers, and addition salts thereof with a pharmaceutically-acceptable acid or base.

10. A compound of claim 1 which is selected from 1-(dimethylaminoethyl)-6-([1,2,4]triazol-4-yl)indole, and an addition salt thereof with a pharmaceutically-acceptable acid.

11. A compound of claim 1 which is selected from 1-(dimethylaminoethyl)-6-([1,2,4]triazol-4-yl)indazole, and an addition salt thereof with a pharmaceutically-acceptable acid.

12. A compound of claim 1 which is selected from 1-{3-[4-(5-methoxypyrimidin-4-yl)piperazin-1-yl]propyl}-6-([1,2,4]triazol-4-yl)indole, and an addition salt thereof with a pharmaceutically-acceptable acid.

13. A compound of claim 1 which is selected from 1-{3-[4-(5-methoxypyrimidin-4-yl)piperazin-1-yl]propyl}-6-([1,2,4]triazol-4-yl)indazole, and an addition salt thereof with a pharmaceutically-acceptable salt.

14. A method for treating a living body afflicted with venous insufficiency, and/or migraine, and/or migraine associated with vascular diseases, comprising the step of administering to the living body an amount of a compound of claim 1 which is effective for alleviation of said conditions.

15. A pharmaceutical composition comprising as active principle an effective amount of a compound of claim 1 in combination with one or more pharmaceutically-acceptable excipients or vehicles.

16. A method for treating a living body afflicted with venous insufficiency, and/or migraine, and/or migraine associated with vascular diseases, comprising the step of administering to the living body an amount of a compound of claim 9 which is effective for alleviation of said condition.

17. A pharmaceutical composition comprising as active principle an effective amount of a compound of claim 9 in combination with one or more pharmaceutically-acceptable excipients or vehicles.

* * * * *

UNITED STATES PATENT AND TRADEMARK OFFICE
CERTIFICATE OF CORRECTION

PATENT NO. : 6,020,336
DATED : February 1, 2000
INVENTOR(S) : G. Lavielle, O. Muller, C. Vayssettes-Courchay, J-J. Descombes, T. Verberuen It is certified that error appears in the above-identified patent and that said Letters Patent is hereby corrected as shown below:

Title Page:
Insert-- [73] Assignee: ADIR ET COMPAGNIE, Courbevoie France --.
Insert -- Attorney, Agent or Firm—The Firm of Gordon W. Hueschen --.

Column 1:
Line 5, delete the word "a".
Line 14: "5-$HT_{1D}$-5-$_{1\text{-like}}$" should read -- 5-$HT_{1D}$-5-$HT_{1\text{-like}}$ --.

Column 3:
Line 19: After "phosphonic acid," insert --acetic acid, trifluoroacetic acid, lactic acid, pyruvic acid, malonic acid, succinic acid, -- and continue....

Column 6:
Line 16: "$G_2$" should read -- $G_1$ --.
Line 24, At the far right hand corner of the formula, "(V)" should read: -- (VI) --.
Line 36, "a compound a" should read --a compund of --.

UNITED STATES PATENT AND TRADEMARK OFFICE
CERTIFICATE OF CORRECTION

PATENT NO.   : 6,020,336
DATED        : February 1, 2000
INVENTOR(S)  : G. Lavielle, O. Muller, C. Vayssettes-Courchay, J-J. Descombes, T. Verbeuen It is certified that error appears in the above-identified patent and that said Letters Patent is hereby corrected as shown below:

Column 8,
Line 16, At the end of the line, "with" should read --from --.
Line 31, "piperiodone." should read -- piperidone. --.

Column 9,
Line 38, "-6-indole" should read -- -indole --.
Line 59, "chlorothy-" should read --chloroethyl- --.

Column 10,
Line 47, "Step a:  (1-" should read -- Step a: 1- (1- --.

Column 13,
Line 20, "1- [1- (2- (2-" should read -- 1- [1-(2- --.
Line 22, "Step a: 1- [1- (2- (2-" should read -- Step a: 1- [1- (2- --.
Line 28, "Step b:  1- [1- (2- (2-"should read -- Step b: 1 - [1- (2- --.
Line 47, "piperid-4-yl) -6-" should read -- piperid -4-yl]-6- --.

UNITED STATES PATENT AND TRADEMARK OFFICE
CERTIFICATE OF CORRECTION

PATENT NO. : 6,020,336
DATED : February 1, 2000
INVENTOR(S) : G. Lavielle, O. Muller, C. Vayssettes-Courchay, J-J. Descombes, T. Verberuen It is certified that error appears in the above-identified patent and that said Letters Patent is hereby corrected as shown below:

Column 17,
Line 1, After the word "in", insert the word -- the --.

Column 22,
Line 62, "test" should read -- tests --.

Column 23,
Line 11, "mount" should read -- mounted --.

Column 24,
Line 31, "$(C_3-C_6)$-" should read -- $(C_3-C_7)$- --.

Column 25,
Line 1, "claim 2" should read: -- claim 1 --.
Line 14, "$(C_3-C_6)$" should read --$(C_3-C_7)$ --.
Line 40, In both instances, "represent" should read -- represents --.

Signed and Sealed this

Third Day of July, 2001

*Attest:*

NICHOLAS P. GODICI
*Attesting Officer*     *Acting Director of the United States Patent and Trademark Office*